United States Patent [19]

Ushikubo et al.

[11] Patent Number: 5,380,933
[45] Date of Patent: Jan. 10, 1995

[54] METHOD FOR PRODUCING AN UNSATURATED CARBOXYLIC ACID

[75] Inventors: Takashi Ushikubo; Hiroya Nakamura, both of Yokohama; Yukio Koyasu; Shin Wajiki, both of Tokyo, all of Japan

[73] Assignee: Mitsubishi Kasei Corporation, Tokyo, Japan

[21] Appl. No.: 187,719

[22] Filed: Jan. 28, 1994

[30] Foreign Application Priority Data

Jan. 28, 1993 [JP] Japan ................................. 5-12616
Jun. 24, 1993 [JP] Japan ................................. 5-153651
Dec. 8, 1993 [JP] Japan ................................. 5-308013

[51] Int. Cl.$^6$ ............................................. C07C 51/16
[52] U.S. Cl. ................................... 562/549; 562/547
[58] Field of Search ................ 562/549, 534, 535, 547

[56] References Cited

U.S. PATENT DOCUMENTS

| | | | |
|---|---|---|---|
| 4,014,925 | 3/1977 | Ferlazzo et al. | 560/208 |
| 4,219,670 | 8/1980 | Okada et al. | 562/546 |
| 4,277,375 | 7/1981 | Decker et al. | 502/241 |
| 4,339,355 | 7/1982 | Decker et al. | 502/343 |
| 4,966,990 | 10/1990 | Otake et al. | 560/214 |
| 5,049,692 | 9/1991 | Hatano et al. | 560/214 |
| 5,231,214 | 7/1993 | Ushikubo et al. | 560/214 |
| 5,281,745 | 1/1994 | Ushikubo et al. | 560/214 |

FOREIGN PATENT DOCUMENTS

| | | |
|---|---|---|
| 0010902 | 5/1980 | European Pat. Off. |
| 2-67236 | 3/1990 | Japan . |
| 3-170445 | 7/1991 | Japan . |

OTHER PUBLICATIONS

Journal of Catalysis, vol. 101, pp. 389–395, 1986, M. AI, "Oxidation of Propane to Acrylic Acid on $V_2O_5$-$P_2O_5$-Based Catalysts".

*Primary Examiner*—Arthur C. Prescott
*Attorney, Agent, or Firm*—Oblon, Spivak, McClelland, Maier & Neustadt

[57] ABSTRACT

A method for producing an unsaturated carboxylic acid, which comprises subjecting an alkane to a vapor phase catalytic oxidation reaction in the presence of a catalyst containing a mixed metal oxide comprising, as essential components, Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$$0.25 < r_{Mo} < 0.98$$

$$0.003 < r_V < 0.5$$

$$0.003 < r_{Te} < 0.5$$

$$0.003 < r_X < 0.5$$

wherein $r_{Mo}$, $r_V$, $r_{Te}$ and $r_X$ are molar fractions of Mo, V, Te and X, respectively, based on the total amount of the essential components exclusive of oxygen.

13 Claims, No Drawings

METHOD FOR PRODUCING AN UNSATURATED CARBOXYLIC ACID

The present invention relates to a method for producing an unsaturated carboxylic acid by subjecting an alkane to a vapor phase catalytic oxidation reaction. Particularly, the present invention relates to a method particularly suitable for producing acrylic acid or methacrylic acid by vapor phase catalytic oxidation of propane or isobutane, respectively.

Unsaturated carboxylic acids such as acrylic acid and methacrylic acid are industrially important as starting materials for various synthetic resins, coating materials and plasticizers. For the production of an unsaturated carboxylic acid such as acrylic acid or methacrylic acid, a method of catalytically reacting an olefin such as propylene or isobutene with oxygen at a high temperature in a vapor phase in the presence of a catalyst, has been known as the most common method.

On the other hand, in view of the price difference between propane and propylene or between isobutane and isobutene, there is a growing interest in developing a method for producing an unsaturated carboxylic acid such as acrylic acid or methacrylic acid in one step by using a lower alkane such as propane or isobutane as the starting material and by subjecting it to a vapor phase catalytic oxidation reaction in the presence of a catalyst.

As examples of the catalyst for the production of acrylic acid in one step by subjecting propane to a vapor phase catalytic oxidation reaction, a Mo—S-b—P—O type catalyst (European Patent No. 0010902), a V—P—Te—O type catalyst (Journal of Catalysis, Vol. 101, p389 (1986)), a Bi—Mo—O type catalyst and a V—P—Te—O type catalyst (Japanese Unexamined Patent Publication No. 170445/1991) are known. On the other hand, as an example of the catalyst for the production of methacrylic acid in one step by subjecting isobutane to a vapor phase catalytic oxidation reaction, a P—Mo—O type catalyst (Japanese Unexamined Patent Publication No. 145249/1988) is known.

However, each of the methods using such catalysts has a drawback such that the yield of the desired unsaturated carboxylic acid is not adequate, or the reaction system is complex.

The present inventors have conducted various studies on the method for producing an unsaturated carboxylic acid using an alkane such as propane or isobutane as a starting material and as a result have found it possible to produce the desired unsaturated carboxylic acid such as acrylic acid or methacrylic acid in a yield substantially better than the conventional methods by subjecting an alkane such as propane or isobutane to a vapor phase catalytic oxidation reaction in the presence of a catalyst containing a mixed metal oxide comprising molybdenum, vanadium, tellurium and a certain type of metal, whereby the above problems can be solved. The present invention has been accomplished on the basis of this discovery.

Thus, the present invention provides a method for producing an unsaturated carboxylic acid, which comprises subjecting an alkane to a vapor phase catalytic oxidation reaction in the presence of a catalyst containing a mixed metal oxide comprising, as essential components, Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$$0.25 < r_{Mo} < 0.98$$

$$0.003 < r_V < 0.5$$

$$0.003 < r_{Te} < 0.5$$

$$0.003 < r_X < 0.5$$

wherein $r_{Mo}$, $r_V$, $r_{Te}$ and $r_X$ are molar fractions of Mo, V, Te and X, respectively, based on the total amount of the essential components exclusive of oxygen.

Now, the present invention will be described in detail with reference to the preferred embodiments.

The mixed metal oxide to be used as a catalyst component of the present invention comprises Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, as essential components. Among the above elements for X, niobium, tantalum, tungsten and titanium are preferred. Particularly preferred is niobium.

The proportions of the respective essential components, based on the total amount of the essential components exclusive of oxygen, are within the ranges defined by the following formulas:

$$0.25 < r_{Mo} < 0.98$$

$$0.003 < r_V < 0.5$$

$$0.003 < r_{Te} < 0.5$$

$$0.003 < r_X < 0.5$$

wherein $r_{Mo}$, $r_V$, $r_{Te}$ and $r_X$ are molar fractions of Mo, V, Te and X, respectively, based on the total amount of the essential components exclusive of oxygen. For example, when the above mixed metal oxide is represented by the empirical formula $Mo_a V_b Te_c X(1)_d X(2)_e O_n$ wherein X(1) and X(2) represent elements belonging to the above element X, the respective molar fractions will be represented by the following formulas:

$$r_{Mo} = a/(a+b+c+d+e)$$

$$r_v = b/(a+b+c+d+e)$$

$$r_{Te} = c/(a+b+c+d+e)$$

$$r_X = (d+e)/(a+b+c+d+e).$$

As such proportions, the ranges represented by the following formulas are particularly preferred among the above molar fractions:

$$0.35 < r_{Mo} < 0.87$$

$$0.045 < r_V < 0.37$$

$$0.020 < r_{Te} < 0.27$$

$$0.005 < r_X < 0.35.$$

Further, as the mixed metal oxide, the one having a certain specific crystal structure is preferred. Specifically, preferred is the one which exhibits the following five main diffraction peaks at specific diffraction angles $2\theta$ in the X-ray diffraction pattern of the mixed metal oxide (as measured by using Cu—K$\alpha$ ray as the X-ray source):

| X-ray lattice plane | | |
| --- | --- | --- |
| Diffraction angle $2\theta$ ($\pm 0.3°$) | Spacing medium (Å) | Relative intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peak may vary depending upon the measuring conditions of each crystal. However, the relative intensity to the peak intensity at 22.1° being 100, is usually within the above ranges. Generally, the peak intensities at $2\theta = 22.1°$ and 28.2° are distinctly observed. However, so long as the above five diffraction peaks are observable, the basic crystal structure is the same even if other peaks are observed in addition to the five diffraction peaks, and such a structure is useful for the present invention.

The mixed metal oxide can be prepared by the following method. For example, when a mixed metal oxide of the formula $Mo_aV_bTe_cNb_xO_n$ wherein the element X is Nb, is to be prepared, an aqueous solution of telluric acid, an aqueous solution of ammonium niobium oxalate and a solution or slurry of ammonium paramolybdate are sequentially added to an aqueous solution containing a predetermined amount of ammonium metavanadate, so that the atomic ratio of the respective metal elements would be in the prescribed proportions, the mixture is then dried by e.g. evaporation to dryness, spray drying or vacuum drying, and finally the remaining dried product is calcined usually at a temperature of from 350° to 700° C., preferably from 400° to 650° C. usually for from 0.5 to 30 hours, preferably from 1 to 10 hours, to obtain the desired mixed metal oxide.

The above calcination treatment can be conducted in an oxygen atmosphere, but it is preferred to conduct the calcination treatment substantially in the absence of oxygen. Specifically, the treatment is carried out in an inert gas atmosphere of e.g. nitrogen, argon or helium, or in vacuo.

The starting materials for the above mixed metal oxide are not limited to those described above. For example, a wide range of materials including oxides such as $MoO_3$, $V_2O_5$, $V_2O_3$, $TeO_2$ and $Nb_2O_5$, halides or oxyhalides such as $MoCl_5$, $VCl_4$, $VOCl_3$ and $NbCl_5$, alkoxides such as $Mo(OC_2H_5)_5$, $Nb(OC_2H_5)_5$, $VO(OC_2H_5)_3$ and acetylacetone molybdenyl and organometallic compounds, may be used.

A mixed metal oxide thus obtained, exhibits excellent catalytic activities by itself. However, it can be converted to a catalyst having higher activities by grinding such a mixed metal oxide.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be grinded, is rotated, and it includes, for example, a ball mill and a rod mill. The medium-stirring type mill is a wet mill of the type wherein the object to be grinded, contained in a container is stirred by a stirring apparatus, and it includes, for example, a rotary screw type mill, and a rotary disk type mill.

The conditions for grinding may suitably be set to meet the nature of the above-mentioned mixed metal oxide, the viscosity, the concentration, etc. of the solvent used in the case of the wet grinding, or the optimum conditions of the grinding apparatus. However, it is preferred that grinding is conducted until the average particle size of the grinded catalyst precursor would usually be at most 20 $\mu$m, more preferably at most 5 $\mu$m. Remarkable improvement in the catalytic performance can be observed by the grinding to such an extent.

Further, in some cases, it is possible to further improve the catalytic activities by further adding a solvent to the above grinded catalyst precursor to form a solution or slurry, followed by drying again. There is no particular restriction as to the concentration of the solution or slurry, and it is usual to adjust the solution or slurry so that the total amount of the starting material compounds for the grinded catalyst precursor is from 10 to 60 wt %. Then, this solution or slurry is dried by a method such as spray drying, freeze drying, evaporation to dryness or vacuum drying, preferably by spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

The method of the present invention comprises subjecting an alkane to a vapor phase catalytic oxidation reaction in the presence of a catalyst containing the above mixed metal oxide, to produce an unsaturated carboxylic acid.

According to the method of the present invention, it is preferred to employ a starting material gas which contains steam. In such a case, as a starting material gas to be supplied to the reaction system, a gas mixture comprising a steam-containing alkane and an oxygen-containing gas, is usually used. However, the steam-containing alkane and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio of the alkane:oxygen:diluting gas:H₂O in the starting material gas is preferably 1:0.1 to 10.0:0 to 20:0.2 to 70, more preferably 1:1 to 5.0:0 to 10:5 to 40.

When steam is supplied together with the alkane as the starting material gas, the selectivity for an unsaturated carboxylic acid is distinctly improved, and the unsaturated carboxylic acid can be obtained from the alkane in good yield simply by contacting in one stage of the catalyst layer, as is different from the conventional technique where a diluting gas such as nitrogen, argon or helium is added for the purpose of diluting the starting material. However, as a diluting gas to adjust the space velocity, the oxygen partial pressure and the steam partial pressure, an inert gas such as nitrogen, argon or helium may also be used together with steam.

In the present invention, as the starting material alkane it is preferred to employ a $C_{3-8}$ alkane, particularly propane, isobutane or n-butane. As the starting material, propane or isobutane is more preferred. Most preferred is propane. According to the method of the present invention, from such an alkane, an unsaturated carboxylic acid such as an $\alpha,\beta$-unsaturated carboxylic acid can be obtained in good yield. For example, when propane or isobutane is used as the starting material alkane, acrylic acid or methacrylic acid will be obtained, respectively, in good yield.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen to the feed gas, such molecular oxygen may be pure oxygen gas. However, it is usually more economical to use an oxygen-containing gas such as air, since purity is not particularly required.

It is also possible to use only an alkane substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide to the catalyst in the regenerator usually at a temperature of from 300° to 600° C.

The present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 mols, preferably from 0.2 to 18 mols per mol of propane, whereby high selectivity for acrylic acid can be obtained. This reaction can be conducted usually under atmospheric pressure, but may be conducted under a slightly elevated pressure or slightly reduced pressure. With respect to other alkane such as isobutane, the composition of the feed gas may be selected similar to the case of propane.

In the method of the present invention, the reaction temperature is usually from 200° to 550° C., preferably from 300° to 480° C., more preferably from 350° to 440° C., and as compared with the conventional technique, it is possible to produce an unsaturated carboxylic acid in good yield. The gas space velocity SV in the vapor phase reaction is usually within a range of from 100 to 10,000 hr$^{-1}$, preferably from 300 to 6,000 hr$^{-1}$, more preferably from 300 to 2,000 hr$^{-1}$. Further, as a diluting gas to adjust the space velocity and the oxygen partial pressure, an inert gas such as nitrogen, argon or helium may be employed.

When the oxidation reaction of propane is conducted by the method of the present invention, carbon monoxide, carbon dioxide, acetic acid, etc. will be produced as by-products, in addition to acrylic acid, but the amounts of such by-products are very small. Further, in the method of the present invention, an unsaturated aldehyde may sometimes be formed depending upon the reaction conditions. For example, when propane is used as the starting material alkane, acrolein may be formed, and when isobutane is used as the starting material alkane, methacrolein may be formed. In such a case, such an unsaturated aldehyde can be converted to the desired unsaturated carboxylic acid by subjecting it again to the vapor phase catalytic oxidation reaction with the mixed metal oxide-containing catalyst of the present invention or by subjecting it to a vapor phase catalytic oxidation reaction with a conventional oxidation reaction catalyst for an unsaturated aldehyde.

Now, specific embodiments of the present invention will be described in further detail with reference to Examples. However, it should be understood that the present invention is by no means restricted by such specific Examples. In the following Examples, the conversion, the selectivity and the yield are represented by the following formulas:

Conversion (%) = mols of consumed alkane/mols of supplied alkane × 100

Selectivity (%) = mols of formed desired unsaturated carboxylic acid/mols of consumed alkane × n/m × 100

Yield (%) = mols of formed desired unsaturated carboxylic acid/mols of supplied alkane × n/m × 100

In the above formulas, m is the carbon number of the supplied alkane, and n is the carbon number of the formed desired unsaturated carboxylic acid.

EXAMPLE 1

A mixed metal oxide of the empirical formula $Mo_1V_{0.3}Te_{0.23}Nb_{0.12}O_n$ wherein n is determined by the oxidation states of other elements, was prepared as follows.

In 325 ml of warm water, 15.7 g of ammonium metavanadate was dissolved, and 23.6 g of telluric acid and 78.9 g of ammonium paramolybdate were sequentially added thereto to obtain a uniform aqueous solution. Further, 117.5 g of an aqueous solution of ammonium niobium oxalate having niobium concentration of 0.456 mol/kg, was mixed thereto to obtain a slurry. This slurry was heat-treated to remove water and obtain a solid. This solid was molded by a tabletting machine into a tablet of 5 mm in diameter × 3 mm in length, which was then pulverized, sieved to from 16 to 28 mesh and calcined in a nitrogen stream at 600° C. for two hours.

A mixed metal oxide thus obtained was subjected to powder X-ray diffraction analysis (using Cu-Kα ray as the X-ray source) whereby main diffraction peaks were observed at diffraction angles 2θ of 22.1° (100), 28.2° (57.3), 36.2° (16.9), 45.1° (15.2) and 50.0° (10.1) (the numerals in the brackets indicate relative intensity based on the peak intensity of 2θ=22.1° being 100.)

0.37 g of the mixed metal oxide thus obtained was packed into a reactor, and a vapor phase catalytic reaction was conducted by supplying a feed gas in a molar ratio of propane:air=1:15 at a reaction temperature of 400° C. at a space velocity SV of 1,734 hr$^{-1}$. The results are shown in Table 1.

EXAMPLE 2

0.37 g of a mixed metal oxide prepared in the same manner as in Example 1 was packed into a reactor, and a vapor phase catalytic reaction was conducted by supplying a feed gas in a molar ratio of propane:air:nitrogen=1:7.5:7.5 at a reaction temperature of 380° C. at a space velocity SV of 1,734 hr$^{-1}$. The results are shown in Table 1.

EXAMPLE 3

30 g of a mixed metal oxide prepared in the same manner as in Example 1 was grinded in a mortar, and 0.6 g of bismuth hydroxide was further added thereto and mixed. This mixture was molded by a tabletting machine into tablet of 5 mm in diameter×3 mm in length, which was then pulverized, sieved to from 16 to 28 mesh and calcined in a nitrogen stream at 550° C. for two hours. 0.37 g of a mixed metal oxide of the empirical formula $Mo_1V_{0.3}Te_{0.23}Nb_{0.12}Bi_{0.017}O_x$ wherein x is determined by the oxidation states of other elements, thus obtained was packed into a reactor, and a vapor phase catalytic reaction was conducted by supplying a feed gas in a molar ratio of propane:air=1:15 at a reaction temperature of 380° C. at a space velocity SV of 1,854 hr$^{-1}$. The results are shown in Table 1.

EXAMPLE 4

0.55 g of a mixed metal oxide prepared in the same manner as in Example 1 was packed into a reactor, and a vapor phase catalytic reaction was conducted by supplying a feed gas in a molar ratio of propane:air:nitrogen=1:15:14 at a reaction temperature of 390° C. at a space velocity SV of 1,871 hr$^{-1}$. The results are shown in Table 1.

TABLE 1

|  | Conversion of propane (%) | Selectivity for acrylic acid (%) | Yield of acrylic acid (%) |
|---|---|---|---|
| Example 1 | 75.3 | 42.4 | 32.0 |
| Example 2 | 49.8 | 56.2 | 28.0 |
| Example 3 | 63.3 | 48.4 | 30.6 |
| Example 4 | 41.8 | 38.7 | 16.2 |

COMPARATIVE EXAMPLE 1

A mixed metal oxide of the empirical formula $Mo_1V_{0.3}Nb_{0.12}O_n$ wherein n is determined by the oxidation states of other elements, was prepared in the same manner as in Example 1 except that telluric acid was not incorporated.

0.55 g of this mixed metal oxide was packed into a reactor, and a vapor phase catalytic reaction was conducted by supplying a feed gas in a molar ratio of propane:air=1:15 at a reaction temperature of 400° C. at a space velocity SV of 662 hr$^{-1}$. As a result, the conversion of propane was 82.0%, but no formation of acrylic acid was detected.

COMPARATIVE EXAMPLE 2

A mixed metal oxide of the empirical formula $Mo_1V_{0.3}Te_{0.23}O_n$ wherein n is determined by the oxidation states of other elements, was prepared in the same manner as in Example 1 except that the aqueous solution of ammonium niobium oxalate solution was not added.

0.55 g of this mixed metal oxide was packed into a reactor, and a vapor phase catalytic reaction was conducted by supplying a feed gas in a molar ratio of propane:air=1:15 at a reaction temperature of 400° C. at a space velocity SV of 668 hr$^{-1}$. As a result, the conversion of propane was 48.3%, but no formation of acrylic acid was detected.

EXAMPLE 5

0.55 g of a mixed metal oxide prepared in the same manner as in Example 1 was packed into a reactor, and a vapor phase catalytic reaction was conducted by supplying a feed gas in a molar ratio of propane:air:H$_2$O=1:15:14 at a reaction temperature of 390° C. at a space velocity SV of 1,871 hr$^{-1}$. The results are shown in Table 2.

EXAMPLE 6

0.59 g of a mixed metal oxide prepared in the same manner as in Example 1 was packed into a reactor, and a vapor phase catalytic reaction was conducted by supplying a feed gas in a molar ratio of propane:air:H$_2$O=1:15:7 at a reaction temperature of 380° C. at a space velocity SV of 1,439 hr$^{-1}$. The results are shown in Table 2.

EXAMPLE 7

0.55 g of a mixed metal oxide prepared in the same manner as in Example 1 was packed into a reactor, and a vapor phase catalytic reaction was conducted by supplying a feed gas in a molar ratio of propane:air:H$_2$O=1:15:36 at a reaction temperature of 420° C. at a space velocity SV of 3,247 hr$^{-1}$. The results are shown in Table 2.

EXAMPLE 8

30 g of a mixed metal oxide prepared in the same manner as in Example 1 was grinded in a mortar, and the powder was dispersed in 100 ml of water to obtain an aqueous slurry. This slurry was heat-treated to obtain a powdery solid. This solid was molded by a tabletting machine into a tablet of 5 mm in diameter×3 mm in length, which was then pulverized, sieved to from 16 to 28 mesh and calcined in a nitrogen stream at 600° C. for two hours. 0.61 g of a catalyst thus obtained was packed into a reactor, and a vapor phase catalytic reaction was conducted by supplying a feed gas in a molar ratio of propane:air:H$_2$O=1:15:14 at a reaction temperature of 380° C. at a space velocity SV of 1,861 hr$^{-1}$. The results are shown in Table 2.

TABLE 2

|  | Conversion of propane (%) | Selectivity for acrylic acid (%) | Yield of acrylic acid (%) |
|---|---|---|---|
| Example 5 | 65.7 | 58.0 | 38.1 |
| Example 6 | 61.2 | 57.5 | 35.2 |

TABLE 2-continued

| | Conversion of propane (%) | Selectivity for acrylic acid (%) | Yield of acrylic acid (%) |
| --- | --- | --- | --- |
| Example 7 | 69.0 | 52.5 | 36.2 |
| Example 8 | 80.1 | 60.5 | 48.5 |

COMPARATIVE EXAMPLE 3

0.55 g of a mixed metal oxide prepared in the same manner as in Comparative Example 1 was packed into a reactor, and a vapor phase catalytic reaction was conducted by supplying a feed gas in a molar ratio of propane:air:$H_2O$=1:15:14 at a reaction temperature of 400° C. at a space velocity SV of 1,230 hr$^{-1}$. As a result, the conversion of propane was 63.2%, but no formation of acrylic acid was detected.

EXAMPLE 9

0.5 g of a mixed metal oxide prepared in the same manner as in Example 1 was packed into a reactor, and a vapor phase catalytic reaction was conducted by supplying a feed gas in a molar ratio of n-butane:air=1:24 at a reaction temperature of 400° C. at a space velocity SV of 1,000 hr$^{-1}$. The results are shown in Table 3.

EXAMPLE 10

0.5 g Of a mixed metal oxide prepared in the same manner as in Example 1 was packed into a reactor, and a vapor phase catalytic reaction was conducted by supplying a feed gas in a molar ratio of n-butane:air:$H_2O$=1:24:22 at a reaction temperature of 410° C. at a space velocity SV of 1,900 hr$^{-1}$. The results are shown in Table 3.

TABLE 3

| | Conversion of propane (%) | Selectivity for acrylic acid (%) | Yield of acrylic acid (%) |
| --- | --- | --- | --- |
| Example 9 | 83.1 | 9.5 | 7.9 |
| Example 10 | 82.0 | 17.8 | 14.6 |

According to the method of the present invention, the desired unsaturated carboxylic acid can be produced in good yield by a single step method using an alkane as the starting material.

We claim:

1. A method for producing an unsaturated carboxylic acid, which comprises subjecting an alkane to a vapor phase catalytic oxidation reaction in the presence of a catalyst containing a mixed metal oxide comprising, as essential components, Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$0.25 < r_{Mo} < 0.98$
$0.003 < r_V < 0.5$
$0.003 < r_{Te} < 0.5$
$0.003 < r_X < 0.5$ wherein $r_{Mo}$, $r_V$, $r_{Te}$ and $r_X$ are molar fractions of Mo, V, Te and X, respectively, based on the total amount of the essential components exclusive of oxygen.

2. The method according to claim 1, wherein as a starting material gas to be supplied to the reaction system, steam is used together with the alkane.

3. The method according to claim 1 or 2, wherein the catalyst is the one prepared by a method which comprises a step of grinding the mixed metal oxide.

4. The method according to claim 2, wherein the molar ratio of the alkane:oxygen:diluting gas:steam in the starting material gas is 1:0.1 to 10:0 to 20:0.2 to 70.

5. The method according to claim 4, wherein the molar ratio of the alkane:oxygen:diluting gas:steam in the starting material gas is 1:1 to 5.0:0 to 10:5 to 40.

6. The method according to claim 1, wherein the proportions of the respective essential components satisfy the following formulas:

$0.35 < r_{Mo} < 0.87$
$0.045 < r_V < 0.37$
$0.020 < r_{Te} < 0.27$
$0.005 < r_X < 0.35$ wherein $r_{Mo}$, $r_V$, $r_{Te}$ and $r_X$ are as defined in claim 1.

7. The method according to claim 1, wherein the mixed metal oxide exhibits X-ray diffraction peaks at the following diffraction angles 2θ in the X-ray diffraction (using Cu—Kα ray):

Diffraction angle 2θ (±0.3°)
22.1°.
28.2°.
36.2°.
45.2°.
50.0°.

8. The method according to claim 1, wherein X is at least one element selected from the group consisting of niobium, tantalum, tungsten and titanium.

9. The method according to claim 1, wherein X is niobium.

10. The method according to claim 1, wherein the alkane is a $C_{3-8}$ alkane.

11. The method according to claim 1, wherein the alkane is propane, isobutane or n-butane.

12. The method according to claim 1, wherein the alkane is propane or isobutane.

13. The method according to claim 1, wherein the alkane is propane.

* * * * *